United States Patent
Shener-Irmakoglu et al.

(10) Patent No.: US 12,048,416 B2
(45) Date of Patent: Jul. 30, 2024

(54) CANNULA IDENTIFICATION FOR USE WITH FLUID MANAGEMENT

(71) Applicant: Smith & Nephew, Inc., Memphis, TN (US)

(72) Inventors: Cemal Shener-Irmakoglu, Woburn, MA (US); Kenneth W. Krause, Andover, MA (US)

(73) Assignee: SMITH & NEPHEW, INC., Memphis, TN (US)

(*) Notice: Subject to any disclaimer, the term of this patent is extended or adjusted under 35 U.S.C. 154(b) by 881 days.

(21) Appl. No.: 16/494,961

(22) PCT Filed: Apr. 13, 2018

(86) PCT No.: PCT/US2018/027465
§ 371 (c)(1),
(2) Date: Sep. 17, 2019

(87) PCT Pub. No.: WO2018/191600
PCT Pub. Date: Oct. 18, 2018

(65) Prior Publication Data
US 2020/0085286 A1 Mar. 19, 2020

Related U.S. Application Data

(60) Provisional application No. 62/485,004, filed on Apr. 13, 2017.

(51) Int. Cl.
*A61B 1/00* (2006.01)
*A61B 1/015* (2006.01)
(Continued)

(52) U.S. Cl.
CPC .... *A61B 1/00059* (2013.01); *A61B 1/000096* (2022.02); *A61B 1/00016* (2013.01);
(Continued)

(58) Field of Classification Search
CPC . A61B 1/015; A61B 1/00009; A61B 1/00016; A61B 1/00043; A61B 1/00059;
(Continued)

(56) References Cited

U.S. PATENT DOCUMENTS 5,343,855 A * 9/1994 Iida ..................... A61B 1/12
600/157
5,800,383 A 9/1998 Chandler et al.
(Continued)

FOREIGN PATENT DOCUMENTS

| | | | | |
|---|---|---|---|---|
| DE | 102013101158 A1 * | 8/2014 | ............ | A61B 90/90 |
| EP | 3009077 A1 | 4/2016 | | |
| JP | 2010158303 A | 7/2010 | | |

OTHER PUBLICATIONS

European Patent Office as Searching Authority; Search Report and Written Opinion mailed Jul. 3, 2018 for International patent application PCT/US2018/027465 filed Apr. 13, 2018, 16 pages.

*Primary Examiner* — Nathan R Price
*Assistant Examiner* — Tania Ismail
(74) *Attorney, Agent, or Firm* — Dickinson Wright PLLC; Mark E. Scott

(57) ABSTRACT

A surgical system for controlling fluid pressure during a surgical procedure is provided. Example systems include an inflow pump coupled to a fluid source and defining an outlet port. An inflow cannula is coupled to the outlet port of the inflow pump and includes a barcode disposed thereon. An endoscope extends from a proximal end to a distal end and includes a shaft. A camera is coupled at the proximal end of the endoscope and provides visualization of a surgical site through the shaft and output a corresponding imagery signal. A pump control unit is coupled to the inflow pump and controls an outlet pressure of the inflow pump. A camera control unit is coupled to the camera and to the pump control unit and receives the imagery signal and decodes the bar- (Continued)

code and conveys information indicative of a pressure loss across the inflow cannula to the pump control unit.

19 Claims, 7 Drawing Sheets

(51) Int. Cl.
  *A61B 1/045* (2006.01)
  *A61M 5/168* (2006.01)
(52) U.S. Cl.
  CPC ...... *A61B 1/00043* (2013.01); *A61B 1/00071* (2013.01); *A61B 1/00114* (2013.01); *A61B 1/015* (2013.01); *A61B 1/045* (2013.01); *A61M 5/16877* (2013.01); *A61B 1/00009* (2013.01); *A61M 2205/3358* (2013.01); *A61M 2205/3362* (2013.01); *A61M 2205/52* (2013.01); *A61M 2205/6063* (2013.01); *A61M 2205/6072* (2013.01)
(58) Field of Classification Search
  CPC .......... A61B 1/00071; A61B 1/00114; A61M 5/16877; A61M 2025/3344; A61M 1/0058; A61M 2205/6063; A61M 2205/6072; A61M 2205/52; A61M 2205/3358; A61M 2205/3362
  See application file for complete search history.

(56) References Cited

U.S. PATENT DOCUMENTS

| | | | |
|---|---|---|---|
| 6,752,799 B2 * | 6/2004 | Grund | A61M 5/30 604/514 |
| 7,510,542 B2 | 3/2009 | Blight | |
| 8,591,453 B2 | 11/2013 | Stubkjaer et al. | |
| 8,944,051 B2 | 2/2015 | Acker et al. | |
| 9,289,110 B2 | 3/2016 | Woolford et al. | |
| 2005/0014995 A1 * | 1/2005 | Amundson | A61B 90/36 600/105 |
| 2005/0092322 A1 | 5/2005 | Collins, Jr. | |
| 2013/0197471 A1 * | 8/2013 | Williams | A61M 5/365 604/247 |
| 2015/0088091 A1 * | 3/2015 | Beasley | G16H 40/63 604/533 |
| 2015/0343173 A1 | 12/2015 | Tobescu et al. | |
| 2016/0151557 A1 | 6/2016 | Brady et al. | |
| 2017/0007750 A1 * | 1/2017 | Woolford | A61B 1/317 |
| 2017/0165454 A1 * | 6/2017 | Tuohy | A61B 90/39 |

* cited by examiner

CANNULA IDENTIFICATION FOR USE WITH FLUID MANAGEMENT

CROSS-REFERENCE TO RELATED APPLICATIONS

This application is a U.S. National Phase Entry of PCT Application Serial No. PCT/US2018/027465 tiled Apr. 13, 2018 and titled "Cannula Identification for Use with Fluid Management." The PCT application claims the benefit of U.S. Provisional Application Ser. No. 62/485,004 filed Apr. 13, 2017 titled "Cannula Identification for Use with Fluid Management." The PCT application and the provisional application are incorporated by reference herein as if reproduced in full below.

BACKGROUND

One of the main challenges in endoscopic (e.g., arthroscopic) surgery is in delivering sufficient flow and pressure to the surgical site and maintaining a clear view for the surgeon. The sufficient flow and pressure is generally accomplished with an irrigation fluid that is delivered to the surgical site by an inflow pump. A flexible tube commonly connects the inflow pump to an inflow cannula into which an endoscope may be inserted. The endoscope shaft extends coaxially through the inside of the cannula shaft. The annular space between the endoscope shaft and the cannula shaft serves as a path for the irrigation fluid. The annular space is generally quite small in size and therefore creates an area of high resistance to flow. Such high resistance to flow in turn causes a large pressure drop due to frictional loss that can be compensated by the inflow pump in order to maintain a set pressure in the surgical site. Inflow pumps, in many cases, have a pressure sensor that measures the pressure in the tubing either proximally to the pump or distally close to the surgical site but still outside of it. Consequently, the pressure loss through the cannula is not known by the pump, so the pressure either needs to be measured or assumed to be of a given value at a given flow rate. If pressure is to be measured, the pump runs a calibration routine prior to surgery if pressure is to be assumed, the pump is pre-programmed with a set of values.

Calibration routines may be utilized in such situations; however, these routines are typically cumbersome and inaccurate and generally cause unstable or inaccurate flow and pressure parameters in the surgical site. Similarly, pre-programmed settings make too many assumptions that similarly cause unstable and inaccurate flow and pressure conditions.

SUMMARY

There is provided a surgical system for controlling fluid pressure during a surgical procedure. The system includes an inflow pump that defines an inlet port fluidly coupled to a fluid source and also defines an outlet port. An inflow cannula extends along a central axis from a first end to a second end and defines an internal flow path fluidly coupled to the outlet port of the inflow pump. The inflow cannula also includes at least one barcode disposed thereon. An endoscope extends from a proximal end to a distal end and includes a shaft. A camera is coupled at the proximal end of the endoscope and is configured to provide visualization of a surgical site through the shaft and from the distal end and output a corresponding imagery signal. A pump control unit is operatively coupled to the inflow pump and configured to control an outlet pressure developed by the inflow pump at the outlet port. A camera control unit is operatively coupled to the camera and communicatively coupled to the pump control unit and configured to receive the imagery signal from the camera and decode the at least one barcode and convey information indicative of a pressure loss across the inflow cannula to the pump control unit.

In some embodiments, the pump controller is further configured to receive the information indicative of the pressure loss across the inflow cannula from the camera control unit and control the outlet pressure developed by the inflow pump based on the information.

In some embodiments, the inflow cannula has an outward facing surface and the at least one barcode is disposed on the outward facing surface.

In some embodiments, the pump control unit is further configured to calculate the pressure loss via the following expression:

$$\Delta P = aQ^2 + bQ + c$$

wherein Q is a flow rate of the inflow pump and a and b are a pair of coefficients corresponding to the inflow cannula.

In some embodiments, the camera control unit is further configured to extract the pair of coefficients directly from the at least one barcode.

In some embodiments, the at least one barcode includes a plurality of barcodes and the camera control unit includes a coefficient memory storing the pair of coefficients corresponding to each of the plurality of barcodes and the camera control unit is further configured to extract the pair of coefficients indirectly from the one of the plurality of barcodes by determining the pair of coefficients for the one of the plurality of barcodes using the coefficient memory.

In some embodiments, the at least one barcode is a one dimensional barcode.

In some embodiments, the at least one barcode is a two dimensional barcode.

In some embodiments, the shaft of the endoscope is configured to telescope into the second end of the inflow cannula coaxially in the internal flow path to define an annular cavity between the inflow cannula and the shaft.

In some embodiments, a communication cable is disposed between the pump control unit and the camera control unit.

In some embodiments, the pump control unit and the camera control unit are each configured to wirelessly communicate with one another.

There is also provided a method for controlling fluid pressure during a surgical procedure. The method includes the step of scanning a barcode disposed on an inflow cannula coupled to an outlet port of an inflow pump using a camera coupled an endoscope. The method continues by decoding the at least one barcode using a camera control unit operatively coupled to the camera and communicatively coupled to a pump control unit operable to control the inflow pump. The next step of the method is determining information indicative of a pressure loss across the inflow cannula associated the at least one barcode for the inflow cannula. The method concludes by controlling an outlet pressure developed by the inflow pump at the outlet port based on the information using the pump control unit.

In some embodiments, the method further includes the steps of conveying the information to the pump control unit using the camera control unit and receiving the pressure loss information at the pump control unit.

In some embodiments, determining information indicative of the pressure loss across the inflow cannula associated the at least one barcode for the inflow cannula further comprises extracting the pair of coefficients directly from the at least one barcode.

In some embodiments, the at least one barcode further comprises a plurality of barcodes and wherein determining information indicative of the pressure loss across the inflow cannula associated the at least one barcode for the inflow cannula further comprises determining a pair of coefficients for the one of the plurality of barcodes using a coefficient memory of the camera control unit storing the pair of coefficients corresponding to each of the plurality of barcodes.

In some embodiments, the step of scanning the at least one barcode disposed on the inflow cannula coupled to the outlet port of an inflow pump using the camera of the endoscope further comprises outputting a corresponding imagery signal using the camera to the camera control unit and wherein the step of decoding the at least one barcode using the camera control unit operatively coupled to the camera and communicatively coupled to the pump control unit operable to control the inflow pump further comprises receiving the imagery signal from the camera of the endoscope using the camera control unit.

In some embodiments, the method further includes the steps of compensating the pressure loss across the inflow cannula by varying the outlet pressure of the inflow pump and maintaining a desired pressure in a surgical site downstream of the inflow cannula.

Further features and advantages of at least some of the embodiments of the present invention, as well as the structure and operation of various embodiments of the present invention, are described in detail below with reference to the accompanying drawings.

BRIEF DESCRIPTION OF THE DRAWINGS

For a detailed description of example embodiments, reference will now be made to the accompanying drawings in which.

DEFINITIONS

Figure 1:
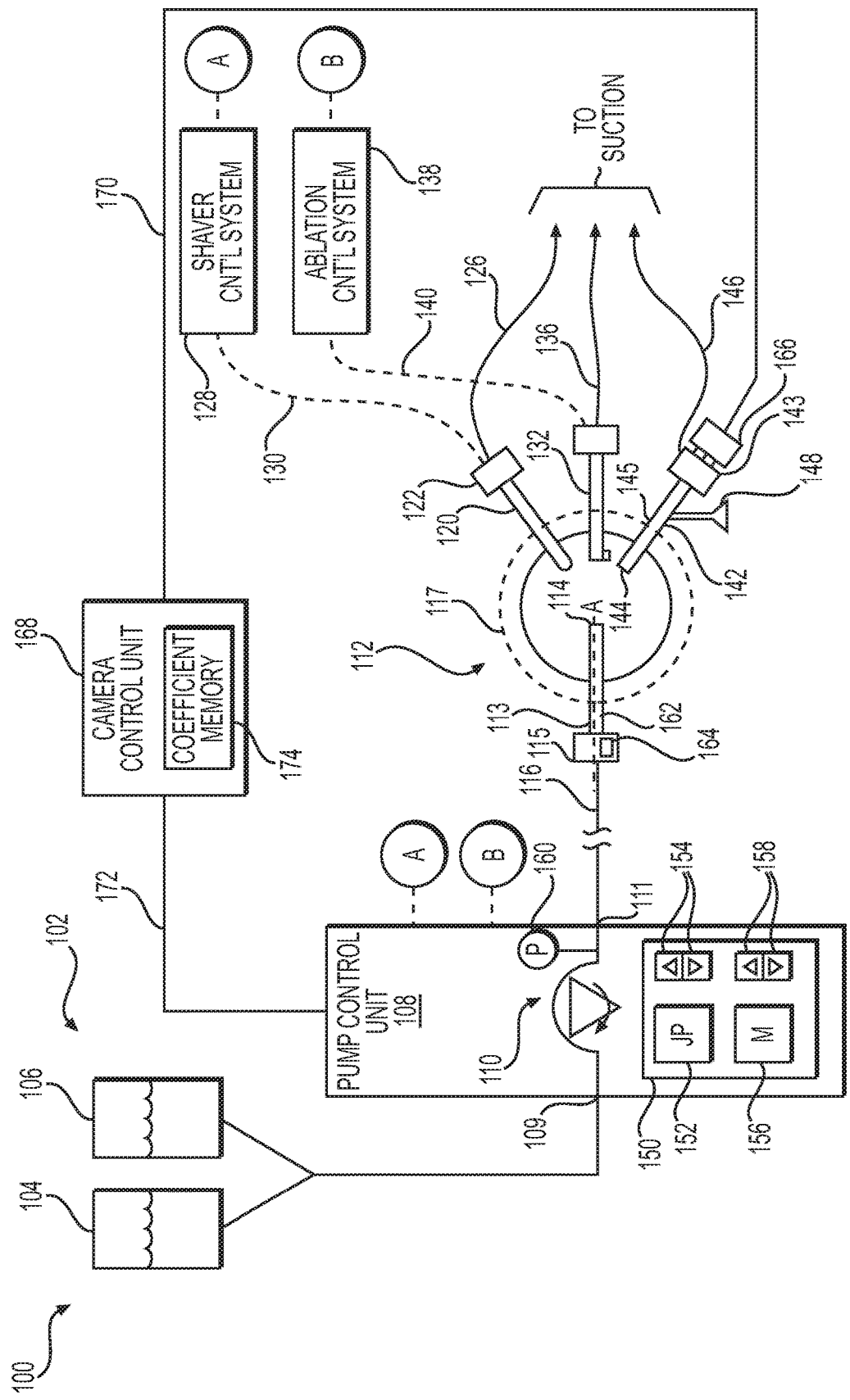
FIG. 1 shows a surgical system in accordance with at least some embodiments.

Various terms are used to refer to particular system components. Different companies may refer to a component by different names—this document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect connection via other devices and connections.

The terms "input" and "output" refer to connections (e.g., electrical, software), and shall not be read as verbs requiring action. For example, a control loop may have a set point input, a feedback input, and a speed control output. In systems implemented directly in hardware, these "inputs" and "outputs" define electrical connections. In systems implemented in software these "inputs" and "outputs" define parameters read by or written by, respectively, the instructions implementing the control loop.

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

In arthroscopic surgery or other endoscopic surgery, for example, a surgical site is irrigated with fluid to maintain visibility for the surgeon, and in some cases to distend the joint space or surgical site. In some example systems, the fluid flow into the surgical site is provided by an inflow pump. In particular, a flexible hose or tubing fluidly couples the inflow pump (e.g., a peristaltic pump) to an inflow cannula that can be used in conjunction with an endoscope to irrigate the surgical site and perform the surgery. Various embodiments are directed to fluid management during such surgical procedures. More particularly, example embodiments described herein are directed to surgical systems that comprise a pump control unit that controls speed of the inflow pump to control pressure of fluid within the surgical site.

Related-art fluid control systems are available from a variety of manufacturers. In most cases, the related-art surgical systems do not directly measure or are not provided a direct measurement of fluid pressure within the surgical site during surgical procedures. Thus, the pump control unit may, for example, infer joint pressure based on pressure of the surgical fluid measured at the outlet of the pump (e.g., inflow pump) and the flow of surgical fluid through the tubing and cannula. Related-art fluid control systems attempt to address the issue using various methods and in some cases, the system may rely on manual control of the inflow pump and/or not try to compensate for any pressure drop across the tubing set.

In other cases in the related art, the relationship of the fluid flow through the tubing set and cannula and pressure drop across the tubing set and cannula is determined based on a calibration procedure performed just prior to the surgical procedure, with the tubing set and cannula to be used in the surgical procedure. The calibration procedure is time consuming, and for a surgical team that does not perform the calibration procedure regularly, the task can be daunting given that mis-calibration can result in over pressure and thus extravasation. Moreover, given the many tubes and devices in the surgical fluid flow path to the surgical site, the calibration is easily mishandled. For example, some surgical implements (e.g., inflow cannula) have fluid flow control valves the surgeon may modulate during surgery. If one of the valves is incorrectly positioned during the calibration procedure (e.g., closed when supposed to be open, or partially closed when supposed to be open), the results of the calibration may be incorrect and yet the surgery may continue with the unrealized associated risks.

FIG. 1 shows a surgical system 100 in accordance with at least some embodiments. In particular, FIG. 1 shows a source of surgical fluid or fluid source 102 in the form of saline bags 104 and 106. The example fluid source 102 fluidly couples to a pump control unit 108 comprising an inflow pump 110, the inflow pump 110 is illustratively shown as a peristaltic pump integrated into the pump control unit 108 and defines an inlet port 109 fluidly coupled to the fluid source 102. The inflow pump 110 also defines a discharge or outlet port 111. It should be understood that the inflow pump 110 may be other types of pumps and may not be a part of the pump control unit 108

In example systems, the surgical fluid is provided to the surgical site 112 by a cannula 113 extending along a central axis A from a first end 114 to a second end 115 and defining an internal flow path fluidly coupled to the outlet port 111 of the inflow pump 110 and to the surgical site 112 through inflow tubing 116. The pressure of fluid within the surgical site 112 may distend the surgical site 112 slightly, such as shown by the dashed line 117 around the surgical site 112. The amount of distention will vary with pressure as well as the rigidity of the tissue surrounding the surgical site 112. The surgical site 112 may be, for example, a knee, a shoulder, a hip, an ankle, or a wrist of the patient.

The example surgical system 100 further comprises a plurality of instruments associated with the surgical site 112 out which fluid may flow; however, various embodiments are applicable to any situation in which surgical fluid flows from the surgical site 112, including surgical fluid flowing directly out an incision through the skin of the patient. The example surgical system 100 comprises a first instrument in the form of a mechanical resection device 120, such as a blade or burr device or "shaver." So as not to unduly complicate the disclosure, the mechanical resection device 120 will be referred to as shaver 120 with the understanding that any mechanical resection device may be used. The shaver 120 may comprise a tubular member that defines an internal channel in communication with a distal opening, and a mechanical blade in operational relationship to the distal opening. The mechanical blade may be turned or oscillated by a motor (e.g., a motor within handle 122). The shaver 120 may be fluidly coupled to a source of suction (e.g., wall suction in a surgical room, a peristaltic pump, or other vacuum pump) by way of tube 126, and may be electrically coupled to a shaver control system 128 by way of an electrical connection 130 (electrical connection shown in dashed lines in FIG. 1 to avoid confusion with tubular connections). In operation, the shaver control system 128 provides electrical energy to the motor in the handle 122, which motor oscillates or turns the mechanical blade at the distal tip. The mechanical blade and distal opening may be placed proximate to tissue to be removed or resected, and the mechanical blade motion may cut the tissue and thereby create tissue fragments. Moreover, the tissue fragments and fluid within the joint may be drawn through the channel inside the shaver 120 by tube 126. In some example systems, the shaver control system 128 may be electrically coupled (shown by bubble "A") to the pump control unit 108 such that the pump control unit 108 can proactively respond to activation of the shaver 120.

Another example instrument that may be used is an ablation device. In particular, the example surgical system 100 further comprises an ablation device 132. The ablation device 132 may comprise a tubular member that defines an internal channel in communication with a distal opening, and a metallic electrode in operational relationship to the distal opening and disposed within the surgical site 112. The ablation device 132 may be fluidly coupled to a source of suction (e.g., wall suction in a surgical room, or a peristaltic pump) by way of tube 136, and may be electrically coupled to an ablation control system 138 by way of an electrical connection 140 (shown with a dashed line). In operation, the ablation control system 138 provides electrical energy to the metallic electrode, which creates plasma near the metallic electrode. The metallic electrode and distal opening may be placed proximate to tissue to be removed or resected, and the plasma may volumetrically reduce and/or disassociate the tissue, creating tissue fragments and ablation by-products. Moreover, the tissue fragments, ablation by-products, and surgical fluid within the surgical site 112 may be drawn through the channel inside the ablation device 132 by way of tubing 136. In some example systems, the ablation control system 138 may be electrically coupled (shown by bubble "B") to the pump control unit 108 such that the pump control unit 108 can proactively respond to activation of the ablation device 132.

Before proceeding, it is noted that while theoretically possible to have both a shaver 120 and ablation device 132 inserted into the surgical site 112 at the same time, in many cases only one such instrument will be used, or will be used at any given time, and thus it is possible that a single entry point through the patient's skin into the surgical site 112 may be created and used for both the example classes of instruments. The instrument the surgeon chooses to use may be inserted into the entry point, used within the surgical site 112, and then withdrawn such that the second instrument can be inserted and used.

Still referring to FIG. 1, an endoscope 142 is also shown. The endoscope 142 extends from a proximal end 143 to a distal end 144 and includes a shaft 145 that defines an internal channel in communication with an opening at the distal end 144. Like the cannula, the endoscope can also be disposed within the surgical site 112. The endoscope 142 may also fluidly couple to a source of suction (e.g., wall suction in a surgical room, or a peristaltic pump) by way of tube 146 to provide an outflow of fluid from the surgical site 112. Thus, the endoscope 142 may be used to ensure fluid flow through surgical site 112. The endoscope 142 also comprises optics for visualizing the inside of the surgical site 112, the optics illustrated by eyepiece 148 associated with the endoscope 142. The endoscope 142 may be utilized separately from the inflow cannula 113 or can be inserted into the inflow cannula 113. Specifically, the shaft 145 of the endoscope 142 is configured to telescope into the second end 115 of the inflow cannula 113 in the internal flow path to define an annular cavity between the inflow cannula 113 and the shaft 145. While the endoscope 142 may provide outflow, outflow can alternatively be provided through a different cannula, for example.

Figure 2:
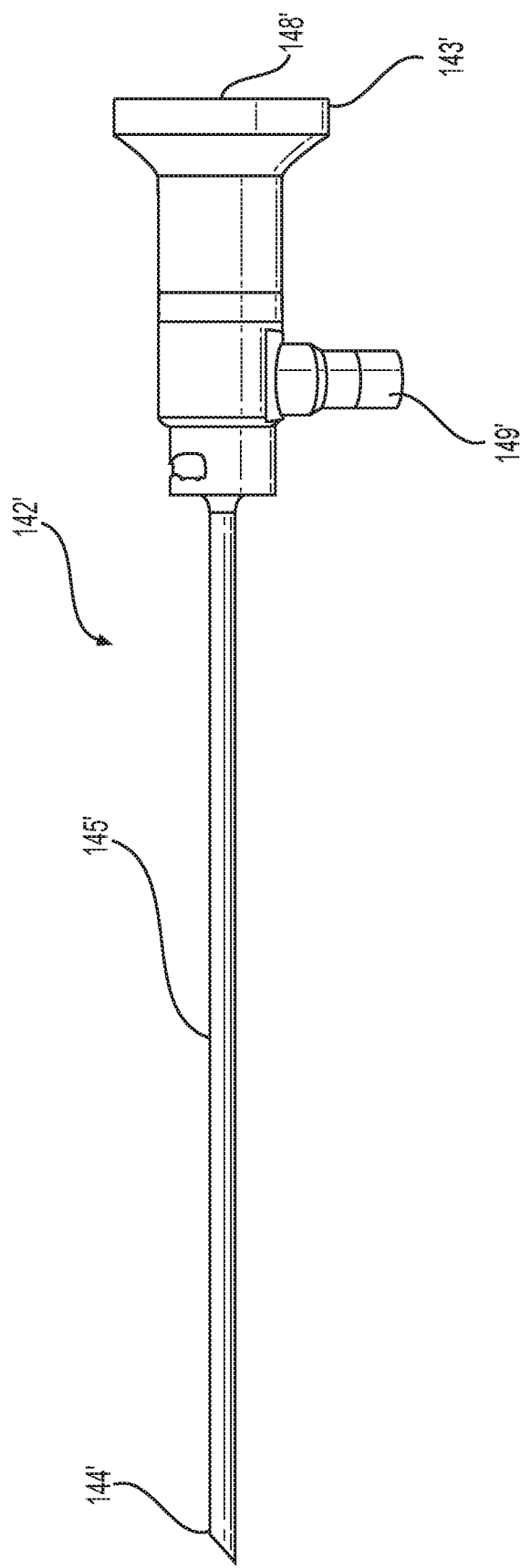
FIG. 2 shows an endoscope in accordance with at least some embodiments.

FIG. 2 shows a side-elevation view of an endoscope in accordance with at least some embodiments. In particular, FIG. 2 shows another example endoscope 142' extending from a proximal end 143' to a distal end 144' and including a shaft 145' that defines an internal channel in communication with an opening at the distal end 144' is shown in FIG. 2; however, unlike endoscope 142 shown in FIG. 1, endoscope 142' does not couple to a source of suction. In addition, the eyepiece 148' of endoscope 142' is disposed at the proximal end 143'. The endoscope 142' also includes a light source port 149' extending transversely therefrom. It should be understood that various configurations of endoscopes 142, 142' may be utilized.

Still referring to FIG. 1, and returning to the pump control unit 108, the example pump control unit 108 further comprises a user interface 150 visible on or through an exterior surface of the pump control unit 108. The user interface 150 may take any suitable form, such as a display device (e.g., liquid crystal display (LCD)) with touch screen capabilities, or individually implement buttons and devices to display values. In the example system, the user interface 150 is designed and constructed to accept a setpoint joint pressure, as shown by setpoint joint pressure window 152 and buttons 154. Thus, by interfacing with the buttons 154 the surgeon may select a setpoint joint pressure as shown in the setpoint joint pressure window 152. Further in example embodiments, the user interface 150 is designed and constructed to accept an indication of a mode of operation of the pump control unit, as shown by mode window 156 and buttons 158. Thus, by interfacing with the buttons 158 the surgeon may select various modes and otherwise adjust settings of the pump control unit 108.

As discussed above, the surgical system 100 may not directly measure pressure in the joint or surgical site 112 and therefore it is advantageous for any pressure losses to be properly taken into consideration. The pump control unit 108 can calculate or infer a joint pressure based on a pressure of surgical fluid measured at the outlet port 111 of the inflow pump 110 (e.g., as measured by pressure sensor 160); however, pressure losses become especially apparent when the shaft 145 of the endoscope 142 is coaxially telescoped within the inflow cannula 113 (i.e., coaxial with central axis A), the annular cavity between the outside surface of the shaft 145 of the endoscope 142, 142' and the inside surface of the inflow cannula 113 (defining the internal flow path) may be quite small in size and creates resistance to fluid flow. The resistance to fluid flow causes a pressure drop due to frictional loss. So, it is beneficial if the pressure created by the inflow pump 110 can be controlled, accounting for the pressure drop the inflow cannula 113, to maintain a desired pressure within the joint space or surgical site 112 as in the embodiments described herein. In system 100, pressure can be measured by the pressure sensor 160. Alternatively, the pressure could be measured in the tubing proximally to the inflow pump 110 or distally close to the surgical site 112. Then, since the pressure loss through the inflow cannula 113 can be determined, the system 100 can compensate the pressure produced by the inflow pump 110 to achieve the desired pressure within the surgical site 112.

In more detail, the pressure loss through the inflow cannula 113 is a function of flow velocity and hence the flow rate, and can be described by a second order polynomial function (a single variable quadratic function) shown in Eq. 1 below:

$$\Delta P = aQ^2 + bQ + c \quad \text{Eq. 1}$$

where $a \neq 0$ and $c = 0$ (no height differential between inflow cannula 113 and inflow pump 110), and where $\Delta P$ is the pressure loss, $Q$ is the flow rate, and $a$ and $b$ are the coefficients unique to a given inflow cannula 113. For example, if the inflow cannula 113 and inflow pump 110 are not placed at the same height (i.e., $c \neq 0$), the difference in height may also need to be taken into account when calculating the pressure loss.

Figure 3:
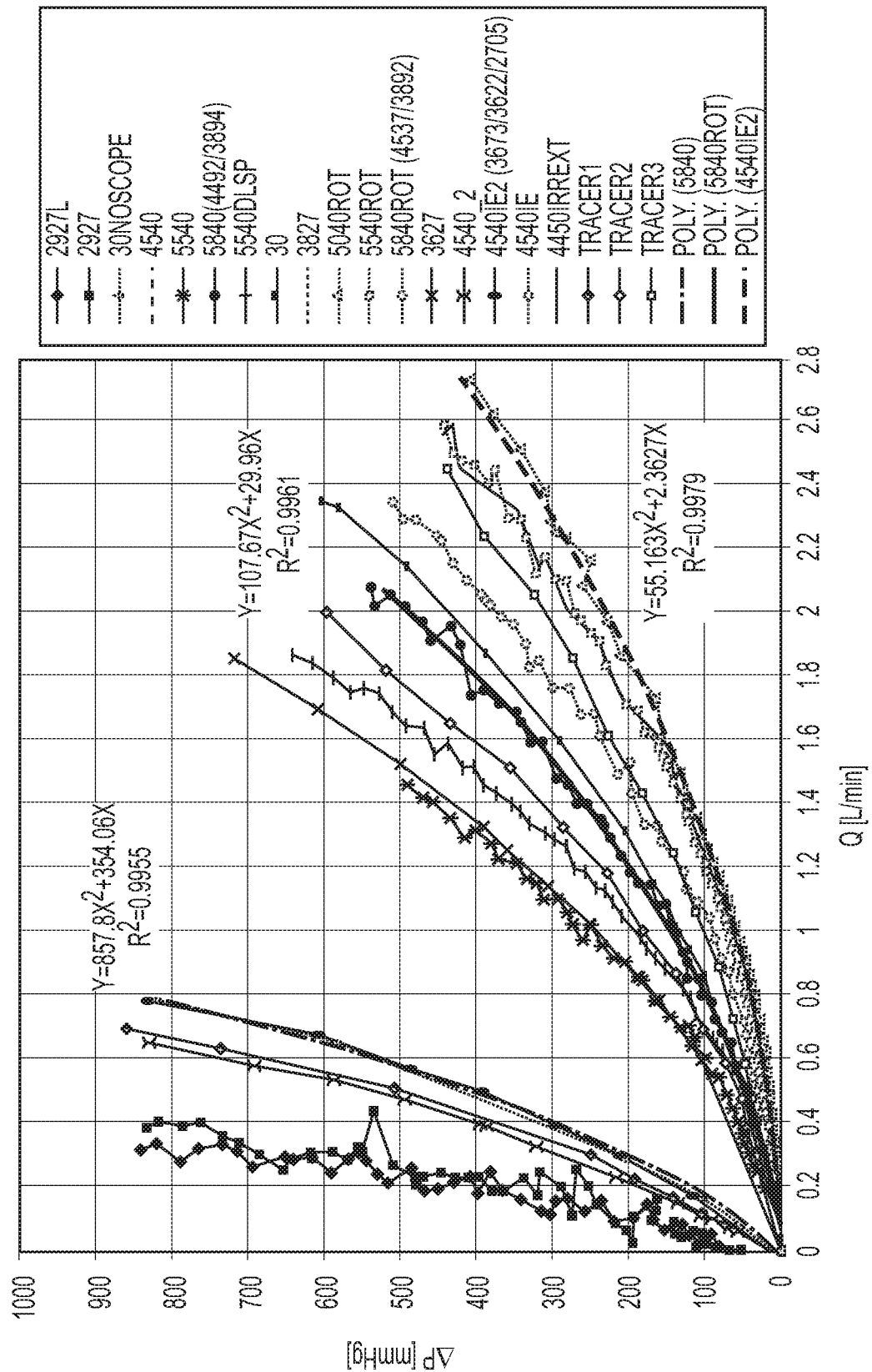
FIG. 3 shows a set of pressure loss curves for example cannulas in accordance with at least some embodiments.

FIG. 3 shows an example a set of pressure loss curves for some of example inflow cannulas (e.g., inflow cannula 113). The flow rate of the inflow pump 110 is either known (e.g., in the case of a peristaltic pump based on pump speed), or measured. In any case, the pump control unit 108 can calculate the pressure loss for any flow rate as long as the pump control unit 108 knows the coefficients a and b. Various embodiments are directed to embedding coefficients a and b, possibly along with other identifying information of the inflow cannula 113, permanently onto the inflow cannula 113, and then retrieving the information prior to surgery and automatically relaying the information to the pump control unit 108.

Figure 4B:
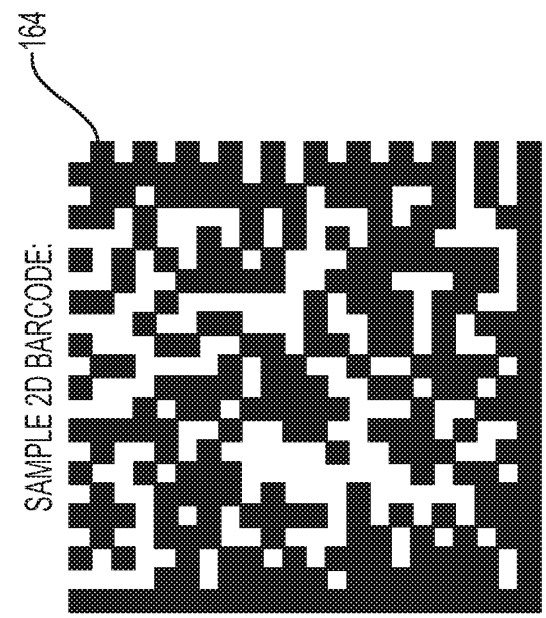
FIGS. 4A and 4B shows example barcodes.
Figure 4A:
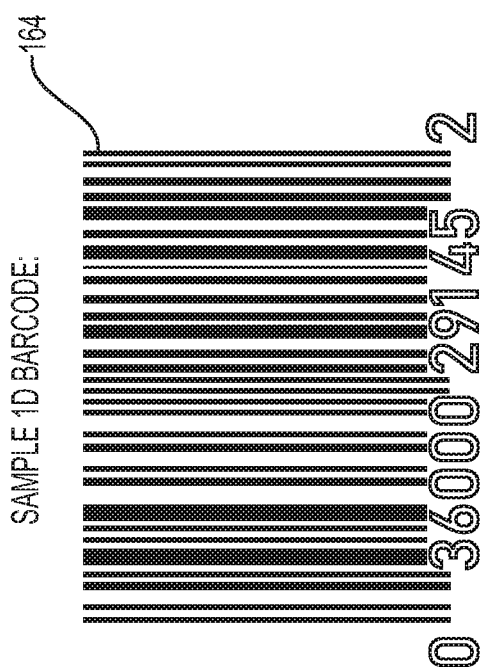

Referring back to FIG. 1, the inflow cannula 113 defines an outward facing surface 162 and at least one barcode 164 is disposed on the outward facing surface 162. FIGS. 4A and 4B show example bar codes in accordance with example embodiments. In particular, in accordance with example embodiments an optical, machine-readable barcode 164 that is either linear (one dimensional, shown in FIG. 4A) type or matrix code (two dimensional, shown in FIG. 4B) type is applied to an outward facing surface 162 of the inflow cannula 113 (e.g., laser marked or etched on). The at least one barcode 164 directly or indirectly contains information about the inflow cannula 113, such as the cannula's coefficients a and b.

The system 100 shown in FIG. 1 further includes a camera 166 coupled at the proximal end 143 of the endoscope 142 that is configured to provide visualization of the surgical site 112 through the shaft 145 and from the distal end 144 and output a corresponding imagery signal. Thus, the camera 166 enables the surgeon to see the operative area within surgical site 112 (e.g., joint space) when the endoscope 142 is telescoped within the inflow cannula 113, for example. In the configuration shown in FIG. 1 the endoscope 142 has yet to be telescoped within the inflow cannula 113. While camera 166 is shown coupled to the proximal end 143 of the endoscope 142, the camera 166 could instead be coupled to the eyepiece 148 or elsewhere on the endoscope 142.

A camera control unit 168 is operatively coupled to the camera 166 (e.g., through camera cable 170) and is communicatively coupled to the pump control unit 108 (e.g., through communication cable 172). The camera control unit 168 is configured to receive the imagery signal from the camera 166 and decode the at least one barcode 164 and convey information indicative of a pressure loss across the inflow cannula 113 to the pump control unit 108. In other words, the camera 166 is used, in example embodiments, to take video or a picture of the at least one barcode 164 associated with the inflow cannula 113. The picture or imagery signal is transmitted to the camera control unit 168 (e.g., by way of camera cable 170). The camera control unit 168 has software enabled to "read" the at least one barcode 164 and extract the coefficient values a and b from the at least one barcode 164, possibly along with other identifying information. The camera control unit 168 then sends the information to the pump control unit 108 (e.g., by way of communication cable 172). Thereafter, the endoscope 142 can be telescoped within the inflow cannula 113 or utilized separately from the inflow cannula 113.

While the camera control unit 168 may be configured to extract the pair of coefficients directly from the at least one barcode 164, the at least one barcode 164 can include a plurality of barcodes 164 (i.e., each one associated with a different inflow cannula 113) and the camera control unit 168 can additionally include a coefficient memory 174 storing the pair of coefficients corresponding to each of the plurality of barcodes 164 (e.g., a lookup table) and the camera control unit 168 is further configured to extract the pair of coefficients indirectly from the one of the plurality of barcodes 164 by determining the pair of coefficients for the one of the plurality of barcodes 164 using the coefficient memory 174.

As discussed above, the pump control unit 108 is operatively coupled to the inflow pump 110 and is configured to control an outlet pressure developed by the inflow pump 110 at the outlet port 111, which is connected to the inflow cannula 113 through inflow tubing 116. Based on the information provided to the pump control unit 108, the pump control unit 108 controls the inflow pump 110 taking into account the pressure drop or pressure loss across the inflow cannula 113 to ensure that the pressure within the surgical site 112 is adequately controlled. So, the pump control unit 108 is further configured to receive the information indicative of the pressure loss across the inflow cannula 113 from the camera control unit 168 and control the outlet pressure developed by the inflow pump 110 based on the information. Though FIG. 1 shows the camera control unit 168 coupled to the pump control unit 108 by communication cable 172, in another embodiments the information determined from the at least one barcode 164 can be sent to the pump control unit 108 wirelessly as long as both devices 108, 168 are connected to the same network or are wirelessly paired to each other.

Figure 5:
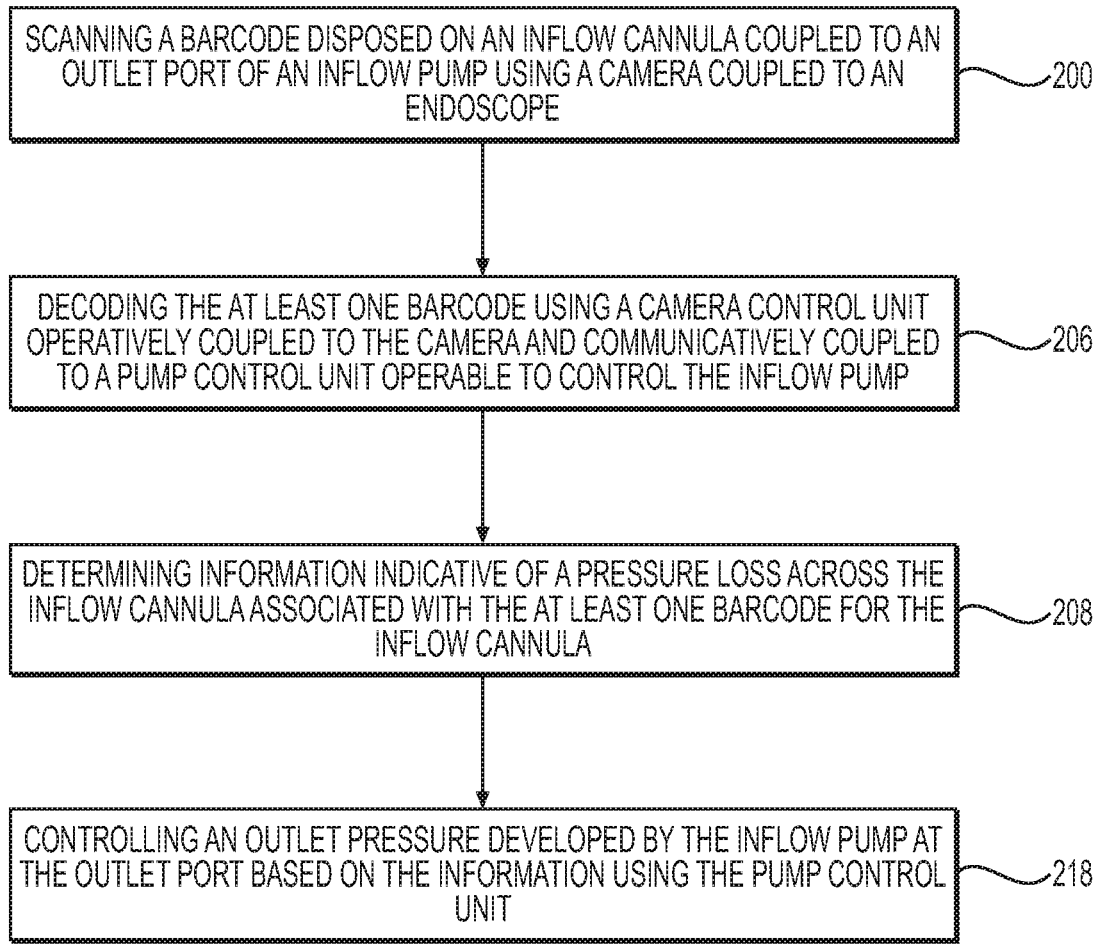
FIG. 5 shows a flow chart illustrating steps of a method for controlling fluid pressure during a surgical procedure in accordance with at least some embodiments.
Figure 6A:
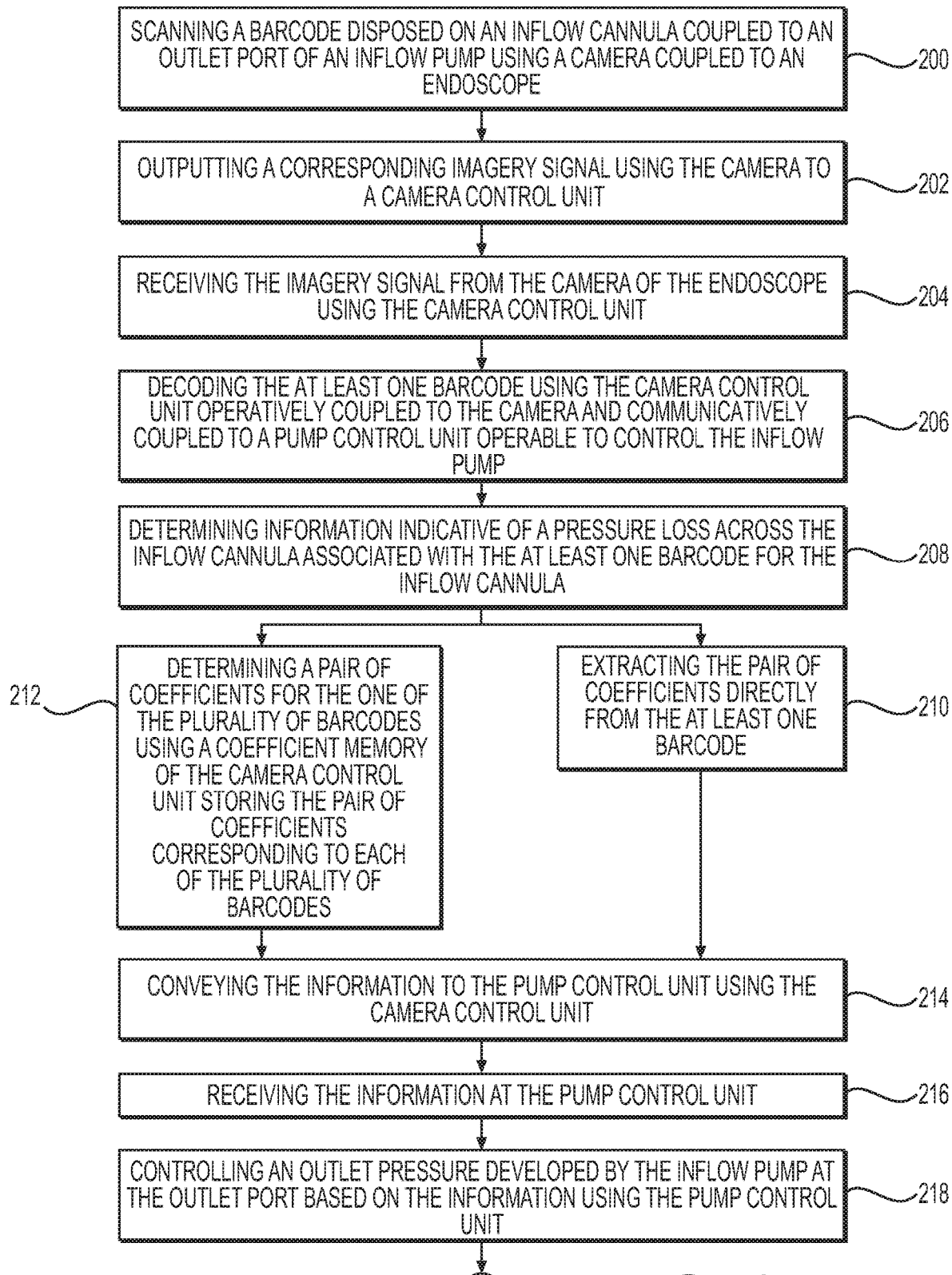
FIGS. 6A and 6B show a flow chart illustrating steps of a method for controlling fluid pressure during a surgical procedure in accordance with at least some embodiments.
Figure 6B:
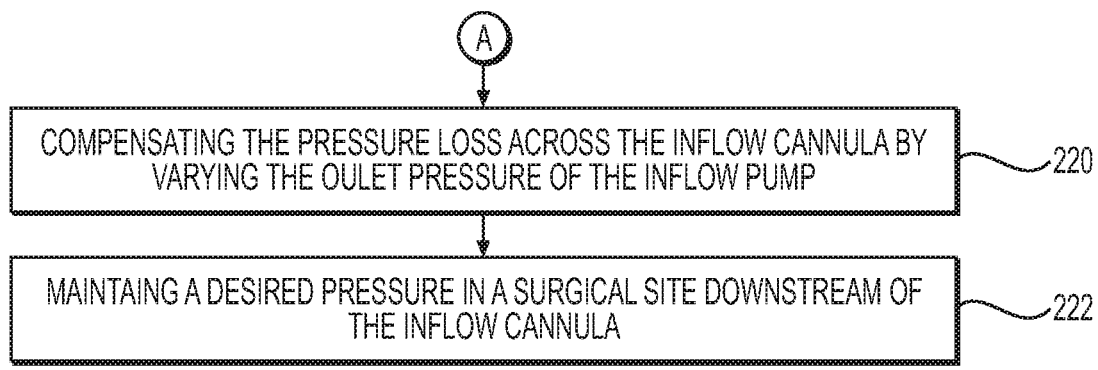

As best shown in FIGS. 5, 6A, and 6B, a method for controlling fluid pressure during a surgical procedure is also provided. The method includes the step of 200 scanning a barcode 164 disposed on an inflow cannula 113 coupled to an outlet port 111 of an inflow pump 110 using a camera 166 coupled to an endoscope 142, 142'. In more detail, such a step can further comprise 202 outputting a corresponding imagery signal using the camera 166 to the camera control unit 168. Again, the at least one barcode 164 can be a one dimensional barcode 164 (FIG. 4A) or a two dimensional barcode 164 (FIG. 4B), for example. The method can proceed by 204 receiving the imagery signal from the camera 166 of the endoscope 142, 142' using the camera control unit 168. The method can then include the step of 206 decoding the at least one barcode 164 using a camera control unit 168 operatively coupled to the camera 166 and communicatively coupled to a pump control unit 108 operable to control the inflow pump 110.

The method then includes the step of 208 determining information indicative of a pressure loss across the inflow cannula 113 associated the at least one barcode 164 for the inflow cannula 113. As discussed above, the pressure loss can calculated by the camera control unit 168 (or the pump control unit 108) via the equation, $\Delta P=aQ^2+bQ+c$, wherein Q is a flow rate of the inflow pump and a and b are a pair of coefficients corresponding to the inflow cannula. The step of 208 determining information indicative of the pressure loss across the inflow cannula 113 associated the at least one barcode 164 for the inflow cannula 113 can further comprise 210 extracting the pair of coefficients directly from the at least one barcode 164. Alternatively, the step of 208 determining information indicative of the pressure loss across the inflow cannula 113 associated the at least one barcode 164 for the inflow cannula 113 can further comprise 212 determining a pair of coefficients for the one of the plurality of barcodes 164 using a coefficient memory 174 of the camera control unit 168 storing the pair of coefficients corresponding to each of the plurality of barcodes 164.

The method can also include the steps of 214 conveying the information to the pump control unit 108 using the camera control unit 168 and 216 receiving the information at the pump control unit 108. Then, the method can continue with the step of 218 controlling an outlet pressure developed by the inflow pump 110 at the outlet port 111 based on the information using the pump control unit 108. Accordingly, the method can include the steps of 220 compensating the pressure loss across the inflow cannula 113 by varying the outlet pressure of the inflow pump 110 and 222 maintaining a desired pressure in a surgical site 112 downstream of the inflow cannula 113.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:

1. A surgical system for controlling fluid pressure during a surgical procedure, comprising:
   an inflow pump defining an inlet port fluidly coupled to a fluid source and defining an outlet port;
   an inflow cannula extending along a central axis from a first end to a second end and defining an internal flow path fluidly coupled to the outlet port of the inflow pump and including an outward-facing surface with at least one machine-readable barcode disposed thereon;
   an endoscope extending from a proximal end to a distal end and including a shaft;
   a camera coupled at the proximal end of the endoscope and configured to provide visualization of a surgical site through the shaft and from the distal end and output a corresponding imagery signal, the at least one machine-readable barcode being viewable by the camera through the shaft of the endoscope;
   a pump control unit operatively coupled to the inflow pump and configured to control an outlet pressure developed by the inflow pump at the outlet port; and
   a camera control unit operatively coupled to the camera and communicatively coupled to the pump control unit and configured to receive the imagery signal from the camera and process the imagery signal to decode the at least one machine-readable barcode received in the imagery signal and based on the decoding extract information associated with the at least one machine-readable barcode indicative of a pressure loss across the inflow cannula not directly measured within the surgical site and convey the information indicative of the pressure loss across the inflow cannula to the pump control unit.

2. The system as set forth in claim 1, wherein the pump controller is further configured to receive the information indicative of the pressure loss across the inflow cannula from the camera control unit and control the outlet pressure developed by the inflow pump based on the information.

3. The system as set forth in claim 1, wherein the pump control unit is further configured to calculate the pressure loss via the following expression:

$$\Delta P=aQ^2+bQ+c$$

wherein Q is a flow rate of the inflow pump and a and b are a pair of coefficients corresponding to the inflow cannula.

4. The system as set forth in claim 3, wherein the camera control unit is further configured to extract the pair of coefficients directly from the at least one machine-readable barcode.

5. The system as set forth in claim 3, wherein the at least one machine-readable barcode includes a plurality of machine-readable barcodes and the camera control unit includes a coefficient memory storing the pair of coefficients corresponding to each of the plurality of machine-readable barcodes and the camera control unit is further configured to extract the pair of coefficients indirectly from the one of the plurality of machine-readable barcodes by determining the pair of coefficients for the one of the plurality of machine-readable barcodes using the coefficient memory.

6. The system as set forth in claim 1, wherein the at least one machine-readable barcode is a one dimensional barcode.

7. The system as set forth in claim 1, wherein the at least one machine-readable barcode is a two dimensional barcode.

8. The system as set forth in claim 1, wherein the shaft of the endoscope is configured to telescope into the second end of the inflow cannula coaxially in the internal flow path to define an annular cavity between the inflow cannula and the shaft.

9. The system as set forth in claim 1, further including a communication cable disposed between the pump control unit and the camera control unit.

10. The system as set forth in claim 1, wherein the pump control unit and the camera control unit are each configured to wirelessly communicate with one another.

11. A method for controlling fluid pressure during a surgical procedure, comprising:
scanning a machine-readable barcode disposed on an outward-facing surface of an inflow cannula coupled to an outlet port of an inflow pump using a camera coupled at a proximal end of an endoscope, the machine-readable barcode being viewable by the camera through the endoscope;
decoding the at least one machine-readable barcode using a camera control unit operatively coupled to the camera and communicatively coupled to a pump control unit operable to control the inflow pump;
based on the decoding, determining information that is associated with the at least one machine-readable barcode, the information being indicative of a pressure loss across the inflow cannula that is not directly measured within the surgical site; and
controlling an outlet pressure developed by the inflow pump at the outlet port based on the information using the pump control unit.

12. The method as set forth in claim 11, further comprising:
conveying the information to the pump control unit using the camera control unit; and
receiving the pressure loss information at the pump control unit.

13. The method as set forth in claim 12, wherein the pressure loss is calculated via the following expression:

$$\Delta P = aQ^2 + bQ + c$$

wherein Q is a flow rate of the inflow pump and a and b are a pair of coefficients corresponding to the inflow cannula.

14. The method as set forth in claim 13, wherein determining information indicative of the pressure loss across the inflow cannula associated the at least one machine-readable barcode for the inflow cannula further comprises extracting the pair of coefficients directly from the at least one machine-readable barcode.

15. The method as set forth in claim 13, wherein the at least one machine-readable barcode further comprises a plurality of machine-readable barcodes and wherein determining information indicative of the pressure loss across the inflow cannula associated the at least one machine-readable barcode for the inflow cannula further comprises determining a pair of coefficients for the one of the plurality of machine-readable barcodes using a coefficient memory of the camera control unit storing the pair of coefficients corresponding to each of the plurality of machine-readable barcodes.

16. The method as set forth in claim 11, wherein scanning the at least one machine-readable barcode disposed on the inflow cannula coupled to the outlet port of an inflow pump using the camera of the endoscope further comprises outputting a corresponding imagery signal using the camera to the camera control unit and wherein the step of decoding the at least one machine-readable barcode using the camera control unit operatively coupled to the camera and communicatively coupled to the pump control unit operable to control the inflow pump further comprises receiving the imagery signal from the camera of the endoscope using the camera control unit.

17. The method as set forth in claim 11, further comprising:
compensating the pressure loss across the inflow cannula by varying the outlet pressure of the inflow pump; and
maintaining a desired pressure in a surgical site downstream of the inflow cannula.

18. The method as set forth in claim 11, wherein the at least one machine-readable barcode is a one dimensional barcode.

19. The method as set forth in claim 11, wherein the at least one machine-readable barcode is a two dimensional barcode.

* * * * *